United States Patent [19]

Ushikubo et al.

[11] Patent Number: 5,149,881
[45] Date of Patent: Sep. 22, 1992

[54] METHOD FOR PRODUCING METHYL ISOBUTYL KETONE

[75] Inventors: Takashi Ushikubo; Yumiko Kakuno, both of Yokohama; Hisako Tsujiura, Chiba, all of Japan

[73] Assignee: Mitsubishi Kasei Corporation, Tokyo, Japan

[21] Appl. No.: 702,401

[22] Filed: May 20, 1991

[30] Foreign Application Priority Data

May 21, 1990 [JP] Japan .................. 2-130553

[51] Int. Cl.$^5$ .............................................. C07C 45/73
[52] U.S. Cl. .................................................. 568/396
[58] Field of Search ............................ 568/388, 396

[56] References Cited

U.S. PATENT DOCUMENTS

| | | | |
|---|---|---|---|
| 3,405,178 | 10/1968 | Wollner et al. | 568/388 |
| 3,666,816 | 5/1972 | Takagi et al. | 568/396 |
| 3,829,495 | 8/1974 | Mizutani et al. | 568/396 |
| 3,953,517 | 4/1976 | Schmitt et al. | 568/396 |
| 4,270,006 | 5/1981 | Heilen et al. | 568/396 |
| 4,289,911 | 9/1981 | Isogai et al. | 568/388 |
| 4,866,210 | 9/1989 | Hoelderich et al. | 568/396 |

FOREIGN PATENT DOCUMENTS

| | | | |
|---|---|---|---|
| 227868 | 7/1987 | European Pat. Off. | 568/388 |
| 251167 | 1/1988 | European Pat. Off. | 568/388 |
| 271182 | 6/1988 | European Pat. Off. | 568/388 |
| 1922755 | 2/1970 | Fed. Rep. of Germany | 568/388 |
| 2900692 | 7/1980 | Fed. Rep. of Germany | 568/388 |
| 2020577 | 7/1970 | France | 568/388 |
| 52-15574 | 6/1977 | Japan | 568/396 |
| 62-258335 | 11/1987 | Japan | 568/396 |
| 8400160 | 1/1984 | World Int. Prop. O. | 568/388 |

OTHER PUBLICATIONS

To et al., Chem. Abst., vol. 105, #99,551b (1986).

Primary Examiner—James H. Reamer
Attorney, Agent, or Firm—Oblon, Spivak, McClelland, Maier & Neustadt

[57] ABSTRACT

A method for producing methyl isobutyl ketone, which comprises contacting acetone and hydrogen in the presence of palladium and a metal oxide and/or metal hydroxide treated with an organosilicon compound of the formula (I):

$$R_a^1(OR^2)_b X_c Si \qquad (I)$$

wherein each of $R^1$ and $R^2$ is a group selected from the group consisting of hydrogen, and alkyl, vinyl and aryl groups having a total carbon number of at most 30, which may have substituents, and $R^1$ and $R^2$ may be the same or different from each other, X is an element selected from the group consisting of hydrogen, fluorine, chlorine, bromine and iodine, and a, b and c are $0 \leq a < 4$, $0 \leq b \leq 4$ and $0 \leq c \leq 4$, respectively, and $a+b+c=4$.

11 Claims, No Drawings

METHOD FOR PRODUCING METHYL ISOBUTYL KETONE

The present invention relates to a method for producing methyl isobutyl ketone by a one step reaction from acetone and hydrogen.

Methyl isobutyl ketone (hereinafter referred to simply as MIBK) is industrially useful as a raw material for e.g. organic solvents, coating materials or stabilizers.

MIBK is industrially produced usually by the following three step process using acetone and hydrogen as starting materials.

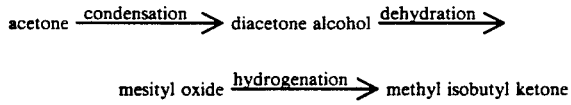

This method is characterized in that the steps of condensation, dehydration and hydrogenation as shown by the above formulas are sequentially conducted and thus the method requires a long process. In the first step, acetone is catalytically reacted in a liquid phase under atmospheric pressure at a temperature of from 10° to 20° C. by means of a solid alkali catalyst such as barium hydroxide to obtain diacetone alcohol. Then, diacetone alcohol obtained by the condensation is separated from unreacted acetone. The separated diacetone alcohol is heated at a temperature of from 100° to 120° C. in a liquid phase in the presence of an acid catalyst such as sulfuric acid or phosphoric acid for dehydration to obtain mesityl oxide. Then, this mesityl oxide is separated and purified, and it is hydrogenated, for example, in the presence of a palladium catalyst to obtain MIBK.

This method is widely used on an industrial scale. However, its process is long including the steps of condensation, dehydration and hydrogenation. Further the operation is cumbersome as it is required to separate intermediates such as diacetone alcohol and mesityl oxide during the process. Further, the condensation reaction from acetone to diacetone alcohol is an equilibrium reaction, and the conversion is as low as about 15%.

Under these circumstances, various studies have been made on a method for producing MIBK directly from acetone and hydrogen in one step. Such a method is very advantageous from the equilibrium point of view, and it is thereby possible to increase the conversion of the raw material per pass. It is economically advantageous over the three step process. The following methods have been reported for the production of MIBK in one step:

(1) a method for synthesizing MIBK using an acid-type ion exchange resin and palladium-carbon as catalysts (German Patent No. 1233453)

(2) a method of using a catalyst having palladium supported on zirconium phosphate (Japanese Examined Patent Publication No. 6994/1974)

(3) a method of using a catalyst having palladium supported on H-type zeolite (Japanese Examined Patent Publication No. 4643/1971)

(4) a method of using palladium-Group IVB metal oxide as catalyst (Japanese Examined Patent Publication No. 15574/1977), and (5) a method of using a palladium-niobic acid catalyst (Japanese Unexamined Patent Publication No. 78745/1986).

However, in these methods, it is impossible to increase the reaction temperature in the case of a resin catalyst, and the preparation of the catalyst is cumbersome. Further, the selectivity for desired MIBK is low, or the catalytic activities are insufficient. Because of these drawbacks, they are not satisfactory from the industrial point of view.

The present inventors have conducted an extensive research to solve such problems of the prior art and to develop a method for producing MIBK in a single step in good yield from acetone and hydrogen. As a result, the present invention has been accomplished.

The present invention provides a method for producing methyl isobutyl ketone, which comprises contacting acetone and hydrogen in the presence of palladium and a metal oxide and/or metal hydroxide treated with an organosilicon compound of the formula (I):

wherein each of $R^1$ and $R^2$ is a group selected from the group consisting of hydrogen, and alkyl, vinyl and aryl groups having a total carbon number of at most 30, which may have substituents, and $R^1$ and $R^2$ may be the same or different from each other, X is an element selected from the group consisting of hydrogen, fluorine, chlorine, bromine and iodine, and a, b and c are $0 \leq a < 4$, $0 \leq b \leq 4$ and $0 \leq c \leq 4$, respectively, and $a+b+c=4$.

Now, the present invention will be described in detail with reference to the preferred embodiments.

The method of the present invention is characterized by contacting acetone and hydrogen in the presence of palladium and a metal oxide and/or metal hydroxide treated with an organosilicon compound of the formula (I):

wherein each of $R^1$ and $R^2$ is a group selected from the group consisting of hydrogen, and alkyl, vinyl and aryl groups having a total carbon number of at most 30, which may have substituents, and $R^1$ and $R^2$ may be the same or different from each other, X is an element selected from the group consisting of hydrogen, fluorine, chlorine, bromine and iodine, and a, b and c are $0 \leq a < 4$, $0 \leq b \leq 4$ and $0 \leq c \leq 4$, respectively, and $a+b+c=4$.

With respect to the organosilicon compound of the above formula (I), each of $R^1$ and $R^2$ is a group selected from the group consisting of (1) hydrogen, (2) an alkyl group having a total carbon number of at most 30, which may have substituents, (3) a vinyl group having a total carbon number of at most 30, which may have substituents, and (4) an aryl group having a total carbon number of at most 30, which may have substituents. The respective substituents may contain a carbon-carbon double bond, and they may further contain hetero atoms such as oxygen, nitrogen, sulfur and silicon.

Further, the organosilicon compound of the formula (I) may be the one wherein a plurality of silicon atoms are linked.

Specific examples of such an organosilicon compound include the following:

| | |
|---|---|
| Trimethylchlorosilane | Me$_3$SiCl |
| Dimethyldichlorosilane | Me$_2$SiCl$_2$ |
| Methyltrichlorosilane | MeSiCl$_3$ |
| Methyldichlorosilane | MeHSiCl$_2$ |
| Dimethylchlorosilane | Me$_2$HSiCl |
| Dimethylvinylchlorosilane | Me$_2$ViSiCl |
| Methylvinyldichlorosilane | MeViSiCl$_2$ |
| Methylchlorodisilane | Me$_n$Si$_2$Cl$_{6-n}$(n = 2 − 3) |
| Triphenylchlorosilane | Ph$_3$SiCl |
| Methyldiphenylchlorosilane | MePh$_2$SiCl |
| Diphenyldichlorosilane | Ph$_2$SiCl$_2$ |
| Methylphenyldichlorosilane | MePhSiCl$_2$ |
| Phenyltrichlorosilane | PhSiCl$_3$ |
| Chloromethyldimethylchlorosilane | ClCH$_2$Me$_2$SiCl |
| Vinyltrichlorosilane | ViSiCl$_3$ |
| γ-chloropropyltrimethoxysilane | Cl(CH$_2$)$_3$Si(OMe)$_3$ |
| γ-chloropropylmethyldichlorosilane | MeCl(CH$_2$)$_3$SiCl$_2$ |
| γ-chloropropylmethyldimethoxysilane | MeCl(CH$_2$)$_3$Si(OMe)$_2$ |
| γ-chloropropylmethyldiethoxysilane | MeCl(CH$_2$)$_3$Si(OEt)$_2$ |
| Methyldimethoxysilane | MeHSi(OMe)$_2$ |
| Methyldiethoxysilane | MeHSi(OEt)$_2$ |
| Dimethylethoxysilane | Me$_2$HSiOEt |

In the above formulas, Me represents a methyl group, Vi represents a vinyl group, Ph represents a phenyl group and Et represents an ethyl group. The same applies hereinafter.

It is preferred to use an organosilicon compound of the formula (I) wherein c=0, i.e. the one which does not contain X. Specific examples of such an organosilicon compound include the following:

| | |
|---|---|
| Trimethylmethoxysilane | Me$_3$SiOMe |
| Trimethylethoxysilane | Me$_3$SiOEt |
| Dimethyldimethoxysilane | Me$_2$Si(OMe)$_2$ |
| Dimethyldiethoxysilane | Me$_2$Si(OEt)$_2$ |
| Methyltrimethoxysilane | MeSi(OMe)$_3$ |
| Tetramethoxysilane | Si(OMe)$_4$ |
| Methyltriethoxysilane | MeSi(OEt)$_3$ |
| Tetraethoxysilane | Si(OEt)$_4$ |
| Vinyltriethoxysilane | ViSi(OEt)$_3$ |
| Dimethylvinylmethoxysilane | Me$_2$ViSiOMe |
| Dimethylvinylethoxysilane | Me$_2$ViSiOEt |
| Methylvinyldimethoxysilane | MeViSi(OMe)$_2$ |
| Methylvinyldiethoxysilane | MeViSi(OEt)$_2$ |
| Diphenyldimethoxysilane | Ph$_2$Si(OMe)$_2$ |
| Phenyltrimethoxysilane | PhSi(OMe)$_3$ |
| Diphenyldiethoxysilane | Ph$_2$Si(OEt)$_2$ |
| Phenyltriethoxysilane | PhSi(OEt)$_3$ |
| γ-Aminopropyltriethoxysilane | H$_2$N(CH$_2$)$_3$Si(OEt)$_3$ |
| N-(β-Aminoethyl)-γ-aminopropyltrimethoxysilane | H$_2$N(CH$_2$)$_2$NH(CH$_2$)$_3$Si(OMe)$_3$ |
| N-(β-Aminoethyl)-γ-aminopropylmethyldimethoxysilane | H$_2$N(CH$_2$)$_2$NH(CH$_2$)$_3$Si(OMe)$_2$ with Me |
| γ-Mercaptopropyltrimethoxysilane | HS(CH$_2$)$_3$Si(OMe)$_3$ |
| γ-Glycidoxypropyltrimethoxysilane | CH$_2$—CHCH$_2$O(CH$_2$)$_3$Si(OMe)$_3$ with epoxide O |
| γ-Glycidoxypropylmethyldimethoxysilane | CH$_2$—CHCH$_2$O(CH$_2$)$_3$Si(OMe)$_2$ with epoxide O, Me |
| γ-Methacryloxypropyltrimethoxysilane | CH$_2$=C(Me)—C(=O)—O(CH$_2$)$_3$Si(OMe)$_3$ |
| γ-Methacryloxypropylmethyldimethoxysilane | CH$_2$=C(Me)—C(=O)—O(CH$_2$)$_3$Si(OMe)$_2$ with Me |
| n-Octyltriethoxysilane | CH$_3$(CH$_2$)$_7$Si(OC$_2$H$_5$)$_3$ |
| n-Dodecyltriethoxysilane | CH$_3$(CH$_2$)$_{11}$Si(OC$_2$H$_5$)$_3$ |
| n-Octadecyltriethoxysilane | CH$_3$(CH$_2$)$_{17}$Si(OC$_2$H$_5$)$_3$ |

On the other hand, the metal oxide and/or metal hydroxide to be used in the present invention is not particularly limited, so long as it is effective for the dimerization of acetone and the dehydration reaction. For example, an oxide and/or hydroxide of at least one element selected from the group consisting of elements of Groups IIA, IIB, IIIA, IIIB, IVA, IVB, VB and VIB of the Periodic Table, may be mentioned. Specifically, it is preferred to employ an oxide and/or hydroxide of a Group IIA element such as Mg or Ca, a Group IIB element such as Zn or Cd, a Group IIIA element such as Al or Ga, a Group IIIB element such as a lanthanide element such as Sc, Y or Ce, a Group IVA element such as Si or Ge, a Group IVB element such as Ti, Zr or Hf, a Group VB element such as Nb or Ta, or a Group VIB element such as Cr, Mo or W. It is more preferred to employ an oxide and/or hydroxide of a Group IVB element such as Ti or Zr, a Group VB element such as Nb, or Si or Al. More specifically, an oxide such as TiO$_2$, SiO$_2$, Al$_2$O$_3$, Nb$_2$O$_5$ or ZrO$_2$, or a hydroxide corresponding thereto, or a compound oxide such as zeolite, may be used. Such metal oxides and metal hydroxides may be prepared by a precipitation method, a thermal decomposition method or an oxidation method, using the salts, the halides or the oxyhalides of the corresponding elements as the starting materials.

The treatment of the metal oxide and/or metal hydroxide with the above mentioned organosilicon compound is carried out in a liquid phase or in a gas phase.

In the case where the treatment is conducted in a liquid phase, it is common to dissolve the organosilicon compound in a solvent such as a hydrocarbon or a halogenated hydrocarbon, then add the metal oxide and/or metal hydroxide thereto, and then leave the mixture to standstill or stir the mixture at room temperature or under heating. It is advisable to remove moisture from the solvent before use in order to reduce the possibility that even the trace amount of water in the solvent tends to react with the organosilicon compound. The concentration of the organosilicon compound to the solvent is usually from 0.01 to 7% by weight, preferably from 0.1 to 30% by weight. Further, the proportion of the metal oxide and/or metal hydroxide to the solution of the organosilicon compound is usually not higher than about 50% by weight, preferably within a range of from 0.1 to 30% by weight. More specifically, a solvent such as toluene or benzene is employed. For example, when toluene is to be used, moisture is removed by distillation or by an addition of a dehydrating agent, and then the organosilicon compound is added and dissolved in the solvent. Then, the metal oxide and/or metal hydroxide is added thereto. With respect to the temperature for the treatment, the treatment can be proceeded even by leaving the mixture to stand at room temperature for long period of time. However, it is preferred to stir the mixture to conduct the treatment uniformly over the entire metal oxide and/or metal hydroxide. Further, it is advantageous to heat the mixture, since it is thereby possible to complete the treatment by the organosilicon compound in a short period of time. For such heating and stirring, it is convenient to heat and reflux the mixture at the boiling point of the organic solvent used. Such heating and refluxing treatment is conducted under atmospheric pressure or, depending upon the solvent, under reduced pressure. The time required for the treatment varies depending upon the temperature, but usually from 1 to 15 hours. Further, when the metal oxide and/or metal hydroxide is treated by the organosilicon compound as described above, it is advantageous to incorporate a very small amount of an acidic or basic substance, specifically a nitrogen-containing organic compound such as trimethylamine, triethylamine, pyridine, piperidine or quinoline, since the treatment is thereby facilitated.

The metal oxide and/or metal hydroxide thus treated with the organosilicon compound, is then separated by filtration from the solution containing the organosilicon compound, then washed with a hydrocarbon, a halogenated hydrocarbon, an alcohol or an ether and then dried under atmospheric pressure or under reduced pressure.

On the other hand, when the treatment with the organosilicon compound is conducted in a gas phase, the organosilicon compound by itself, or the vapor of a solution having the organosilicon compound dissolved in the above mentioned organic solvent, is introduced to the metal compound and/or metal hydroxide in vacuum or in an inert gas to conduct the treatment. The temperature for the treatment and the pressure of the vapor are determined by the organosilicon compound and the vapor pressure of the organic solvent to be used.

Then, the metal oxide and/or metal hydroxide thus treated with the organosilicon compound is physically mixed with palladium such as palladium-carbon, palladium-alumina or palladium black in the reaction system of acetone and hydrogen described hereinafter or outside the reaction system, or palladium is supported on the metal compound and/or metal hydroxide treated with the organosilicon compound as described above and used for the catalytic reaction of acetone with hydrogen. Otherwise, a metal oxide and/or metal hydroxide having palladium preliminarily supported thereon by a usual method is treated by the organosilicon compound as described above, and then used for the catalytic reaction of acetone with hydrogen. The amount of palladium is usually within a range of from 0.001 to 10% by weight, preferably from 0.01 to 5% by weight, relative to the metal oxide and/or metal hydroxide.

The catalytic reaction of acetone with hydrogen according to the method of the present invention can be conducted in a liquid phase or in a gas phase. It is preferably conducted in a liquid phase. As the reaction system, MIBK may be produced by a so-called fixed bed flow reaction whereby palladium and the metal oxide and/or metal hydroxide treated by the organosilicon compound are present in a heat-insulated or isothermic reactor, and acetone and hydrogen are supplied thereto. Otherwise, a substance comprising palladium and the metal oxide and/or metal hydroxide treated by the organosilicon compound may be suspended in acetone, and hydrogen may be blown thereinto to conduct the reaction. In a case where the reaction is conducted by the fixed bed flow reaction, a reaction system such as a trickle system may be employed. In a case where the reaction is conducted by the suspension method, the reaction may be conducted in either a batch system or a continuous system. The reaction temperature is usually within range of from 30° to 250° C., preferably from 80° to 160° C. With respect to the reaction pressure, the reaction is usually conducted under a pressure of from atmospheric pressure to 50 atm, preferably from 5 to 30 atm, although it also depends on the reaction temperature.

Now, the present invention will be described in further detail with reference to Examples. However, it should be understood that the present invention is by no means restricted by such specific Examples.

EXAMPLE 1

(1) Treatment of Zirconyl Hydroxide 5 g of commercially available zirconyl hydroxide was subjected to vacuum evacuation treatment at 100° C. under 0.01 Torr for 2 hours. Into a flask having an internal capacity of 500 ml and equipped with a stirrer, 100 ml of dry toluene, 10 ml of n-octadecyltriethoxysilane and a small amount (2 or 3 drops from a Komagome pipette) of triethylamine were charged, and after forming a uniform solution, zirconyl hydroxide treated by vacuum evacuation as mentioned above, was added thereto. A cooling condenser was provided at the upper portion of the flask, and the interior of the flask was substituted by argon gas. The mixture was heated under stirring and brought to a boiling condition at about 110° C. The boiling condition was maintained for 6 hours, and then the mixture was cooled to room temperature, and the product was separated by filtration from the toluene solution of n-octadecyltriethoxysilane. The product was further washed with toluene and then with methanol, and then dried under atmospheric pressure at 120° C. for 4 hours.

(2) Mixing of Treated Zirconyl Hydroxide With Palladium

To 1 g of zirconyl hydroxide treated as described in (1), 0.05 g of commercially available 2% palladium-active carbon was mixed, and the mixture was subjected to the reaction as described in the following (3).

(3) Production of MIBK by the Reaction of Acetone With Hydrogen

Into a SUS 316 autoclave having an internal capacity of about 100 ml, about 1 g of the mixture of palladium and the zirconyl hydroxide treated with n-octadecyltriethoxysilane, as described in (2) and 40 ml of acetone were charged, heated to 135° C. and reacted for 4 hours while adjusting the total pressure to 9.5 kg/cm$^2$G by hydrogen pressure. During the reaction, hydrogen was continuously supplied to keep the total pressure to the constant level. The reaction solution was cooled and then the catalyst was separated therefrom. The reaction solution was analyzed by gas chromatography. The results are shown in Table 1.

TABLE 1

| Conversion | Selectivity (%) | | | |
|---|---|---|---|---|
| of acetone (%) | MIBK | IPA*1 | DIBK*2 | MC7K*3 |
| 27.0 | 94.9 | 0.4 | 2.0 | 0.4 |

*1 IPA: Isopropylalcohol
*2 DKBK: 2,6-dimethylheptan-4-one (diisobutyl ketone)

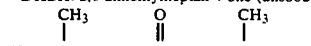

*3 MC7K: 4,6-dimethylheptan-2-one

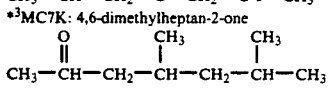

COMPARATIVE EXAMPLE 1

1 g of commercially available zirconyl hydroxide was, without any treatment, mixed with 0.05 g of commercially available 2% palladium-active carbon in the same manner as described in (2) of Example 1, and then the reaction of acetone with hydrogen was conducted in the same manner as described in (3) of Example 1. The conversion of acetone was substantially the same as in Example 1. The selectivity for MIBK was 91.6%, the selectivity for IPA was 0.9%, the selectivity for DIBK was 3.9%, and the selectivity for MC7K was 0.8%.

EXAMPLE 2

In Example 1, using 5 g of titanium hydroxide prepared by hydrolyzing titanium tetra-n-butoxide, instead of zirconyl hydroxide, treatment with n-octadecyl triethoxysilane, mixing with 2% palladium-active carbon and the reaction of acetone with hydrogen were conducted. The conversion of acetone was 29.7%. The selectivities for the respective products are shown in Table 2.

COMPARATIVE EXAMPLE 2

The operation was conducted in the same manner as in Comparative Example 1 except that 1 g of titanium hydroxide as described in Example 2 was sued instead of zirconyl hydroxide. The conversion of acetone was substantially the same as in Example 2. The selectivities for the respective products are shown in Table 2.

EXAMPLE 3

In Example 1, using 5 g of commercially available hydrated niobium oxide instead of zirconyl hydroxide, treatment with n-octadecyltriethoxysilane, mixing with 2% palladium-active carbon ad the reaction of acetone with hydrogen were conducted. The conversion of acetone was 18.0%. The selectivities for the respective products are shown in Table 2.

COMPARATIVE EXAMPLE 3

The same operation as in Comparative Example 1 was conducted except that 1 g of hydrated niobium oxide as described in Example 3 was used instead of zirconyl hydroxide. The conversion of acetone was substantially the same as in Example 3. The selectivities for the respective products are shown in Table 2.

EXAMPLE 4

In Example 1, using 5 g of cerium oxide prepared by thermally decomposing commercially available cerium carbonate at 300° C. in air, instead of zirconyl hydroxide, treatment with n-octadecyltriethoxysilane, mixing with 2% palladium-active carbon and the reaction of acetone with hydrogen were conducted. The conversion of acetone was 32.4%. The selectivities for the respective products are shown in Table 2.

COMPARATIVE EXAMPLE 4

The same operation as in Comparative Example 1 was conducted except that 1 g of cerium oxide as described in Example 4 was used instead of zirconyl hydroxide. The conversion of acetone was substantially the same as in Example 4. The selectivities for the respective products are shown in Table 2.

TABLE 2

| | Metal oxide or metal hydroxide | Selectivity (%) | | | |
|---|---|---|---|---|---|
| | | MIBK | IPA | DIBK | MC7K |
| Example 2 | Titanium hydroxide | 91.4 | 0.0 | 4.9 | 1.0 |
| Comparative Example 2 | | 81.5 | 0.1 | 6.9 | 1.1 |
| Example 3 | Hydrated niobium oxide | 93.5 | 2.5 | 1.7 | 0.4 |
| Comparative Example 3 | | 87.0 | 6.9 | 2.8 | 0.6 |
| Example 4 | Cerium oxide | 95.0 | 0.0 | 2.3 | 0.8 |
| Example 4 | | 94.3 | 0.2 | 2.8 | 1.1 |

EXAMPLE 5

The operation was conducted in the same manner as in Example 1 except that n-dodecyltriethoxysilane was used instead of n-octadecyltriethoxysilane. The results are shown in Table 3.

EXAMPLE 6

The operation was conducted in the same manner as in Example 1 except that n-octyltriethoxysilane was used instead of n-octadecyltriethoxysilane. The results are shown in Table 3.

EXAMPLE 7

The operation was conducted in the same manner as in Example 1 except that diphenyldimethoxysilane was used instead of n-octadecyltriethoxysilane. The results are shown in Table 3.

TABLE 3

| Example No. | Conversion of acetone (%) | Selectivity (%) | | | |
|---|---|---|---|---|---|
| | | MIBK | IPA | DIBK | MC7K |
| 5 | 24.7 | 93.7 | 0.9 | 1.9 | 0.4 |
| 6 | 24.0 | 94.1 | 0.7 | 1.5 | 0.3 |
| 7 | 26.2 | 95.6 | 0.3 | 2.0 | 0.5 |

EXAMPLE 8

Palladium was supported on commercially available zirconyl hydroxide in an amount of 0.1% by weight as palladium. Such zirconyl hydroxide having palladium supported thereon was treated with n-octadecyltriethoxysilane in the same manner as in Example 1.

1 ml (24–60 mesh) of this catalyst was packed in a SUS reaction tube having an inner diameter of 8 mm and acetone and hydrogen were introduced into the reaction tube at supply rates of 12 ml/hr (LHSV=12 $h^{-1}$) and 12.2 Nml/min, respectively, at a reaction temperature of 120° C. under a total pressure (hydrogen pressure) of 9 kg/cm²G to conduct a flow reaction.

According to the results of reaction after 10 hours, the conversion of acetone was 31.3%, the selectivity for MIBK was 93.2%, the selectivity for IPA was 0.6%, the selectivity for DIBK was 3.0%, and the selectivity for

According to the method of the present invention, methyl isobutyl ketone can be produced from acetone and hydrogen economically advantageously with a high selectivity.

We claim:

1. A method for producing methyl isobutyl ketone, which comprises contacting acetone and hydrogen in the presence of palladium and an oxide and/or a hydroxide of at least one metal selected from the group consisting of Group IVB and Group VB elements treated with an organosilicon compound of the formula (I):

wherein each of $R^1$ and $R^2$ is selected from the group consisting of hydrogen, alkyl, vinyl and aryl having a total carbon number of at most 30, wherein $R^1$ may be substituted with groups selected from the group consisting of hydroxyl, amino, alkyl substituted amino, mercapto, glycidoxy, carboxyl and carbonyl and $R^1$ and $R^2$ may be the same or different, X is an element selected from the group consisting of hydrogen, fluorine, chlorine, bromine, and iodine, and a, b and c are such that $0 \leq a < 4$, $0 \leq b \leq 4$ and $0 \leq c \leq 4$, respectively, and $a+b+c=4$.

2. The method according to claim 1, wherein the organosilicon compound is of the formula (I) wherein $c=0$.

3. The method according to claim 1, wherein treatment of the metal oxide and/or metal hydroxide with the organosilicon compound of the formula (I) comprises adding a metal oxide and/or metal hydroxide to a solution prepared by dissolving an organosilicon compound of the formula (I) in a solvent, followed by separation for recovery.

4. The method according to claim 3, wherein an acidic or basic substance is present during the treatment.

5. The method according to claim 1, wherein treatment of the metal oxide and/or metal hydroxide with the organosilicon compound of the formula (I) comprises introducing the organosilicon compound of the formula (I) in its vapor state to a metal oxide and/or metal hydroxide.

6. The method according to claim 1, wherein the palladium and the metal oxide and/or metal hydroxide treated with the organosilicon compound of the formula (I) are present in such a form that the palladium is supported on the metal oxide and/or metal hydroxide.

7. The method according to claim 1, wherein the palladium and the metal oxide and/or metal hydroxide treated by the organosilicon compound of the formula (I) are present in such a form that the metal oxide and/or metal hydroxide having palladium preliminarily supported thereon is treated by the organosilicon compound.

8. The method according to claim 1, wherein the palladium and the metal oxide and/or metal hydroxide treated with the organosilicon compound of the formula (I) are supplied in a mixed state to the catalytic reaction of acetone with hydrogen.

9. The method according to claim 1, wherein the catalytic reaction of acetone with hydrogen is a liquid phase reaction.

10. The method according to claim 1, wherein the catalytic reaction of acetone with hydrogen is a fixed bed flow reaction.

11. The method according to claim 1, wherein the catalytic reaction of acetone with hydrogen is conducted at a temperature of from 30° to 250° C. under a pressure of from atmospheric pressure to 50 atm.